United States Patent [19]

Pennetreau

[11] Patent Number: 5,396,001
[45] Date of Patent: Mar. 7, 1995

[54] PROCESS FOR THE PURIFICATION OF 1,1-DIFLUOROETHANE

[75] Inventor: Pascal Pennetreau, Rixensart, Belgium

[73] Assignee: Solvay (Société Anonyme), Brussels, Belgium

[21] Appl. No.: 155,652

[22] Filed: Nov. 22, 1993

[30] Foreign Application Priority Data

Dec. 2, 1992 [BE] Belgium .............................. 09201057

[51] Int. Cl.⁶ .............................................. C07C 17/38
[52] U.S. Cl. .................................................... 870/179
[58] Field of Search .......................................... 570/179

[56] References Cited

U.S. PATENT DOCUMENTS

| 3,862,995 | 1/1975 | Martens et al. . |
| 4,950,816 | 8/1990 | Tung et al. . |

FOREIGN PATENT DOCUMENTS

| 766395 | 4/1971 | Belgium . | |
| 0370688A1 | 5/1990 | European Pat. Off. . | |
| 0389334 | 9/1990 | European Pat. Off. | 570/179 |
| 0433129A2 | 6/1991 | European Pat. Off. . | |
| 2215019 | 11/1972 | Germany . | |
| 3072437 | 3/1991 | Japan | 570/179 |

*Primary Examiner*—Alan Siegel
*Attorney, Agent, or Firm*—Spencer, Frank & Schneider

[57] ABSTRACT

Purification of crude 1,1-difluoroethane (HFA-152a) from vinyl chloride, by bringing into contact with an active carbon.

10 Claims, No Drawings

PROCESS FOR THE PURIFICATION OF 1,1-DIFLUOROETHANE

The present invention relates to the purification of 1,1-difluoroethane. It more particularly relates to a process for the purification of crude 1,1-difluoroethane from vinyl chloride.

1,1-difluoroethane is particularly advantageous as a substitute for certain chlorofluorocarbons, in particular as a substitute for dichlorodifluoromethane (CFC-12).

1,1-difluoroethane can be prepared by reacting vinyl chloride with hydrogen fluoride, as is described in Patent BE-766,395 on behalf of SOLVAY. In such a process, the mixture of reaction products contains, at the outlet of the hydrofluorination reactor, besides 1,1-difluoroethane, hydrogen chloride arising from the removal of the chlorine atom from the starting compound, unreacted vinyl chloride and unreacted hydrogen fluoride, optionally inert diluents, as well as small amounts of various by-products, mainly a small amount of 1-chloro-1-fluoroethane and vinyl fluoride. Although the reaction is commonly carried out with an excess of hydrogen fluoride with respect to the vinyl chloride, unreacted vinyl chloride always remains in the mixture of reaction products. Whereas the majority of the constituents of the mixture of reaction products can easily be completely separated by distillation, complete separation between vinyl chloride and 1,1-difluoroethane is very difficult to carry out by distillation, these two compounds in fact having boiling points which are relatively close.

The subject of the present invention is a process for the purification of 1,1-difluoroethane which makes it possible efficiently to remove vinyl chloride therefrom.

The invention consequently relates to a process for the purification of crude 1,1-difluoroethane, which is characterized in that the said crude 1,1-difluoroethane is brought into contact with an active carbon.

Crude 1,1-difluoroethane is understood to denote 1,1-difluoroethane contaminated by vinyl chloride. The vinyl chloride content in the crude 1,1-difluoroethane is generally greater than 20 ppm. Most often, it exceeds 50 ppm, indeed 100 ppm. In principle, the crude 1,1-difluoroethane subjected to the process according to the invention can contain significant amounts of vinyl chloride, for example of the order of several percent by weight. In practice, the crude 1,1-difluoroethane does not commonly contain more than 10,000 ppm of vinyl chloride. The crude 1,1-difluoroethane can additionally contain other impurities, such as hydrogen chloride, hydrogen fluoride, vinyl fluoride and 1-chloro-1-fluoroethane. The total amount of these other impurities does not generally exceed 1% by weight of the crude 1,1-difluoroethane. Most often, this amount is less than 0.5% by weight. These other impurities which can be present in the crude 1,1-difluoroethane commonly arise from the process for the manufacture of 1,1-difluoroethane by reacting vinyl chloride with hydrogen fluoride. They can easily be separated from the 1,1-difluoroethane, for example by distillation.

The process according to the invention must be carried out at a suitable temperature, generally from approximately $-25°$ C. to approximately $+100°$ C. It is preferably carried out at a temperature from approximately $-15°$ C. to approximately $+60°$ C. In a particularly preferred way, it is carried out at a temperature from $-10°$ C. to $+20°$ C. The process according to the invention must be carried out at a suitable pressure, generally from approximately 50 kPa to approximately 2000 kPa. Preferably, the process is carried out at a pressure from approximately 100 kPa to approximately 1000 kPa.

The nature of the active carbon used in the process according to the invention does not appear critical. The active carbons conventionally used for the adsorption of vapours or liquids can be used. Good results were obtained in the process according to the invention with various active carbons having a high specific surface, greater than 500 $m^2/g$, preferably at least equal to 750 $m^2/g$. Generally, the specific surface of the active carbon does not exceed 2000 $m^2/g$. Good results were obtained with active carbons having a specific surface not exceeding 1500 $m^2/g$.

The active carbon is used in the form of a powder, the optimum size of the particles of which depends on the conditions under which the process is implemented. Generally, an active carbon is selected in which the diameter of the particles varies from approximately 0.1 mm to 10 mm. The process is preferably carried out with particles with a diameter less than or equal to 3 mm. In a particularly preferred way, particles with a diameter less than or equal to 1.5 mm are used. Moreover, it is preferable to use an active carbon in which the particles have a diameter greater than or equal to 0.2 mm. Very good results were obtained with an active carbon with a particle size of 0.25–1 mm.

The crude 1,1-difluoroethane and the active carbon can be brought into contact according to various techniques well known to one skilled in the art, in any suitable equipment. The operation can be carried out in a fluidized bed but it is generally preferably to arrange the active carbon in the form of a stationary bed of particles, through which a stream of crude 1,1-difluoroethane to be purified is made to pass. This stream can be liquid or gaseous.

When the process is carried out in the gaseous phase, a contact time between the crude 1,1-difluoroethane and the active carbon of at least 1 s is produced. The processing is preferably carried out with a contact time greater than 2 s. Good results were obtained with a contact time greater than or equal to approximately 3 s. In principle, it is possible to work with a very long contact time, for example of several minutes. In practice, for reasons of efficiency, the processing is generally carried out with a contact time of less than 1 minute, preferably less than or equal to approximately 30 s.

When the process is carried out in the liquid phase, a contact time between the crude 1,1-difluoroethane and the active carbon of at least approximately 2 minutes is produced. The processing is preferably carried out with a contact time greater than approximately 5 minutes. In principle, it is possible to work with a very long contact time, for example 120 minutes. In practice, the processing is generally carried out with a contact time of less than 60 minutes, preferably less than or equal to approximately 30 minutes.

When the process is implemented in a stationary bed, the contact time is defined as the ratio of the volume of the bed of active carbon to the flow rate, by volume, of the stream of crude 1,1-difluoroethane. When the process is implemented in a fluidized bed, the contact time is defined as the ratio of the volume of the vessel containing the active carbon to the flow rate, by volume, of the stream of crude 1,1-difluoroethane.

At the conclusion of the process, the active carbon can be regenerated by heating at moderate temperature, for example from 100° to 250° C., under a gaseous stream, for example under nitrogen, or under reduced pressure.

The process according to the invention applies to any crude 1,1-difluoroethane composition contaminated by vinyl chloride. It finds a specific application in the purification of 1,1-difluoroethane obtained by the reaction between vinyl chloride and hydrogen fluoride.

The process according to the invention makes it possible to purify crude 1,1-difluoroethane until a residual vinyl chloride content of less than 1 ppm by weight is obtained.

The following examples illustrate the invention.

EXAMPLES 1 TO 4

A bed of active carbon dried beforehand at 150° C. under a stream of nitrogen, and then under vacuum, for 24 h was placed in a 15 cm$^3$ glass column (length=12.5 cm, diameter=1.25 cm), maintained at 25° C. at atmospheric pressure. A gaseous stream of crude 1,1-difluoroethane consisting of a synthetic mixture of 1,1-difluoroethane (HFA-152a) and of vinyl chloride (VC), containing 3,050 mg of VC per kg, is made to pass through the active carbon. The purified effluent was analysed by in-line gas phase chromatography (detection limit for VC: 20 mg/kg) and the test was continued until the active carbon was saturated with VC (VC content in the gaseous stream at the inlet=VC content in the gaseous stream at the outlet). The flow rate of the gaseous stream during the test was measured by means of a gas meter placed at the outlet of the column. At the end of the test, the active carbon was weighed in order to determine, by the difference from the weight of the active carbon before the test, the total amount of VC and of HFA-152a adsorbed. This quantity, expressed in g/kg of active carbon (A.C.), corresponds to the total adsorption capacity. The VC adsorption capacity of the active carbon was determined on the basis of the gas phase chromatography analyses carried out in-line. Table 1 collates the results of Examples 1 to 4 carried out at a temperature of 25° C. and a residence time of 13 to 15 s with four different active carbons. In Example 1, Norit ® PK carbon from the firm Norit was used. In Examples 2 to 4, Calgon PCB ® active carbon, Calgon CPG ® active carbon and Calgon OL ® active carbon from the company Calgon were used respectively. Besides the VC adsorption capacity and the total adsorption capacity, this table also shows the minimum residual VC content ([VC] min) which it was-possible to achieve during the test in the gaseous stream after passing through the active carbon, as well as an estimation of the selectivity of adsorption of the VC, expressed in % and corresponding to the ratio of the VC adsorption capacity to the total adsorption capacity (VC/total).

EXAMPLES 5 AND 6

Example 1 was repeated with Norit PK active carbons of various particle sizes. The results of these tests, carried out at room temperature, are collated in Table 2.

TABLE 2

| Example | Particle size (mm) | Residence time (s) | [VC] min (mg/kg) | Adsorption capacity (g/kg A.C.) VC | Total |
|---|---|---|---|---|---|
| 5 | 1–3 | 13 | 60–70 | 14.4 | 175 |
| 6 | 3–5 | 12 | 70 | 14.5 | 220 |

The results shown in Table 2 do not show any significant difference in adsorption capacity between the various particle sizes. However, the comparison of these examples with Example 1 shows that fine particle sizes (less than 1 mm) make it possible to achieve a markedly lower residual VC content than the larger particle sizes.

EXAMPLES 7 TO 10

These examples are used to illustrate the influence of temperature on the efficiency of the process. To this end, Example 1 was repeated at various temperatures. The results of these tests are collated in Table 3.

TABLE 3

| Ex. | Temperature (°C.) | Residence time (s) | [VC] min (mg/kg) | Adsorption capacity (g/kg A.C.) VC | Total | VC/total (%) |
|---|---|---|---|---|---|---|
| 7 | −10 | 16 | <25 | 23.4 | 270 | 11.5 |
| 8 | 0 | 14 | <25 | 20.3 | 245 | 8.3 |
| 9 | 50 | 14 | 50 | 9.7 | 170 | 5.7 |
| 10 | 75 | 14 | 125 | 7.1 | 140 | 5.1 |

It is observed that a lowering in the temperature leads to an increase in the total adsorption capacity and, surprisingly, to a relatively more significant increase in the VC adsorption capacity, which is reflected by an increase in the selectivity of adsorption of the VC.

EXAMPLE 11

Example 8 was repeated with a gaseous stream of crude HFA-152a consisting of a synthetic mixture of HFA-152a, vinyl chloride (VC) and vinyl fluoride (VF), containing 180 mg of VC and 490 mg of VF per kg of the mixture. The purified effluent was analysed by in-line gas phase chromatography, with a detection limit for VC of 1 mg/kg. In these conditions, a minimum residual VC content ([VC] min) lower than 1 mg/kg was obtained, while VF was not selectively adsorbed relative to HFA-152a.

I claim:
1. A process for the purification of crude 1,1-difluoroethane by removing vinyl chloride, comprising:

TABLE 1

| Ex. | Active carbon (A.C.) | Particle size (mm) | Residence time (s) | [VC] min (mg/kg) | Adsorption capacity (g/kg A.C.) VC | total = VC + HFA-152A | VC/total (%) |
|---|---|---|---|---|---|---|---|
| 1 | Norit PK | 0.25–1 | 17 | <20 | 14.9 | 240 | 6.2 |
| 2 | Calgon PCB | 2.4–4.8 | 15 | 50 | 12 | 350 | 3.4 |
| 3 | Calgon CPG | 0.4–1.7 | 15 | 30 | 10.2 | 300 | 3.4 |
| 4 | Calgon OL | 0.3–0.85 | 13 | 40 | 10 | 320 | 3.1 | contacting crude 1,1-difluorethane with an active carbon powder at a temperature from about −15° C. to about 60° C., to adsorb vinyl chloride in said crude 1,1-difluoroethane on said active carbon, and separating said vinyl chloride adsorbed on said active carbon from said 1,1-difluoroethane.

2. The process according to claim 1, wherein the crude 1,1-difluoroethane contains from 100 to 10,000 ppm by weight of vinyl chloride.

3. The process according to claim 1, wherein the process is carried out at a temperature from approximately −10° C. to approximately +20° C.

4. The process according to claim 3, wherein the process is carried out at a temperature of 25° C.

5. The process according to claim 1, wherein the process is carried out at a pressure from approximately 50 kPa to approximately 2000 kPa.

6. The process according to claim 1, wherein the active carbon is arranged in the form of a stationary bed of particles, through which the crude 1,1-difluoroethane is made to pass.

7. The process according to claim 1, wherein the crude 1,1-difluoroethane in the liquid form is brought into contact with the active carbon for a time from approximately 2 minutes to approximately 120 minutes.

8. The process according to claim 1, wherein the crude 1,1-difluoroethane in the gaseous state is brought into contact with the active carbon for a time from approximately 3 s to approximately 30 s.

9. The process according to claim 1, wherein an active carbon is selected in which the diameter of the particles varies from 0.2 to 3 mm.

10. The process according to claim 1, wherein the crude 1,1-difluoroethane is obtained by the reaction between vinyl chloride and hydrogen fluoride.

* * * * *